(12) United States Patent
Reed et al.

(10) Patent No.: US 11,203,139 B2
(45) Date of Patent: Dec. 21, 2021

(54) MEDICAL DEVICE WITH OVERMOLDED ADHESIVE PATCH AND METHOD FOR MAKING SAME

(71) Applicant: Becton, Dickinson and Company, Franklin Lakes, NJ (US)

(72) Inventors: Jeffrey Reed, Minden, NE (US); John Knight, Clay Center, NE (US); Scott Townsend, Holdrege, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 304 days.

(21) Appl. No.: 15/840,403

(22) Filed: Dec. 13, 2017

(65) Prior Publication Data

US 2019/0176380 A1 Jun. 13, 2019

(51) Int. Cl.
| | |
|---|---|
| *B29C 45/16* | (2006.01) |
| *B29C 45/14* | (2006.01) |
| *A61M 5/158* | (2006.01) |
| *B29L 31/00* | (2006.01) |
| *A61M 5/142* | (2006.01) |

(52) U.S. Cl.
CPC ......... *B29C 45/1671* (2013.01); *A61M 5/158* (2013.01); *B29C 45/14336* (2013.01); *B29C 45/14786* (2013.01); *A61M 5/14248* (2013.01); *A61M 2005/1586* (2013.01); *A61M 2207/00* (2013.01); *B29L 2031/7548* (2013.01)

(58) Field of Classification Search
None
See application file for complete search history.

(56) References Cited

U.S. PATENT DOCUMENTS

| | | |
|---|---|---|
| 5,384,174 A | 1/1995 | Ward et al. |
| 6,121,611 A | 9/2000 | Lindsay et al. |
| 6,134,461 A | 10/2000 | Say et al. |
| 6,175,752 B1 | 1/2001 | Say et al. |
| 6,560,471 B1 | 5/2003 | Heller et al. |
| D488,230 S | 4/2004 | Ignotz et al. |
| 6,746,582 B2 | 6/2004 | Heller et al. |
| 7,070,580 B2 | 7/2006 | Nielsen |

(Continued)

FOREIGN PATENT DOCUMENTS

| | | |
|---|---|---|
| EP | 2692374 A1 | 2/2014 |
| WO | WO-2008082854 A1 | 7/2008 |

(Continued)

OTHER PUBLICATIONS

3M Science. Applied to Life. Adhesive for when duration matters (Aug. 2017).

(Continued)

*Primary Examiner* — Monica A Huson
(74) *Attorney, Agent, or Firm* — Dickinson Wright PLLC (57) ABSTRACT

An adhesive patch is secured to an infusion set, patch pump or other on-body medical device by an overmolding process during manufacture of the medical device, or during manufacture of a portion of the medical device, without the need for a separate adhesive. This provides a more secure connection between the patch and the medical device, and reduces the required number of adhesive layers from two (skin attachment side and device attachment side) to one (skin attachment side only), thereby simplifying the design and manufacture of the patch.

19 Claims, 5 Drawing Sheets

(56) References Cited

U.S. PATENT DOCUMENTS

| | | |
|---|---|---|
| 7,129,389 B1 | 10/2006 | Watson |
| 7,621,395 B2 | 11/2009 | Mogensen et al. |
| 7,850,658 B2 | 12/2010 | Faust et al. |
| 8,790,311 B2 | 7/2014 | Gyrn |
| 9,501,043 B2 * | 11/2016 | Heck .................... G04G 17/08 |
| 9,795,777 B2 | 10/2017 | Sonderegger et al. |
| 9,889,255 B2 | 2/2018 | Sonderegger et al. |
| 2006/0015063 A1 * | 1/2006 | Butikofer ........... A61M 39/1011 |
| | | 604/93.01 |
| 2008/0167620 A1 | 7/2008 | Adams et al. |
| 2008/0278332 A1 | 11/2008 | Fennell et al. |
| 2010/0198034 A1 | 8/2010 | Thomas et al. |
| 2011/0060196 A1 * | 3/2011 | Stafford ............... A61B 5/6833 |
| | | 600/309 |
| 2014/0316379 A1 * | 10/2014 | Sonderegger ......... A61M 5/142 |
| | | 604/506 |
| 2015/0241288 A1 * | 8/2015 | Keen ..................... G01L 1/16 |
| | | 361/761 |
| 2016/0095597 A1 | 4/2016 | Belson et al. |
| 2016/0310665 A1 | 10/2016 | Hwang et al. |
| 2016/0324470 A1 * | 11/2016 | Townsend ............. G06F 1/163 |

FOREIGN PATENT DOCUMENTS

| | | |
|---|---|---|
| WO | WO-2015095639 A1 | 6/2015 |
| WO | WO-2016026028 A1 | 2/2016 |

OTHER PUBLICATIONS

3M Technical Information Sheet—Product No. 1776—3M TM Medical Nonwoven Tape (2013).

* cited by examiner

MEDICAL DEVICE WITH OVERMOLDED ADHESIVE PATCH AND METHOD FOR MAKING SAME

FIELD OF THE INVENTION

The present invention relates generally to medical devices and to methods for making such devices. In particular, but not by way of limitation, the present invention relates to an infusion set, patch pump or other on-body medical device having an adhesive patch which is secured to the medical device by an overmolding process during manufacture of the medical device or during manufacture of a portion of the medical device.

BACKGROUND OF THE INVENTION

In the management of diabetes, insulin can be administered to a user on a continuous basis using a programmable infusion pump. The pump is small, portable and battery-operated, and can be worn or carried inconspicuously by the user. The pump is attached by a length of tubing to an infusion set, which is a disposable body-worn device having a skin-adhering base, a fluid connector, and a rigid needle or flexible catheter that conducts the insulin into the subcutaneous or intradermal layer of the user's skin. A flexible adhesive patch or pad on the bottom of the infusion set base allows for temporary skin attachment during the period (typically a few days) that the infusion set remains in place before it is removed and replaced for sanitary reasons.

Another type of insulin infusion device, known as a patch pump, has also come into use. Unlike a conventional infusion pump, a patch pump is an integrated device that combines most or all of the required components in a single housing and does not require the use of a separate infusion set or connecting tubing. A patch pump adheres directly to the skin, contains insulin in an internal reservoir, and delivers the insulin via an integrated subcutaneous catheter. As in the case of an infusion set, a patch pump typically includes a flexible adhesive patch on its bottom surface to allow for temporary skin attachment at the infusion site.

The flexible adhesive patch is typically made of a thin fibrous material, similar to a medical dressing, but with adhesive layers on both sides. On the skin contact side, an adhesive suitable for medical or surgical use is provided, and is covered by a removable backing layer or release liner made of silicone-coated kraft paper. The release liner is removed by the user before attaching the infusion set or patch pump to the skin. The skin contact adhesive must be sufficiently strong to secure the infusion set or patch pump to the skin, but must also allow for removal of the device without damaging the skin. On the device side, a different adhesive is used, one which provides for permanent attachment between the patch and the base of the infusion set or patch pump.

Unfortunately, the need to provide two different adhesives complicates the design and manufacture of the patch, and the selection of adhesives and patch materials is limited because not all adhesives and patch materials are compatible with each other. In addition, the manufacturing process for the infusion set or patch pump may require that the adhesive patch be dispensed from a continuous roll for handling by automated equipment. This may impose additional requirements on the types of adhesives that can be used.

SUMMARY OF THE INVENTION

In accordance with the present invention, an adhesive patch is secured to an infusion set, patch pump or other on-body medical device by an overmolding process during manufacture of the medical device, or during manufacture of a portion of the medical device, without the need for a separate adhesive. This provides a more secure connection between the patch and the medical device, and reduces the required number of adhesive layers from two (skin attachment side and device attachment side) to one (skin attachment side only), thereby simplifying the design and manufacture of the patch.

In one aspect, the present invention provides an on-body medical device comprising a molded plastic base and a flexible fibrous, textured, perforated or porous patch having a skin-contacting adhesive on one side and an opposite side overmolded with the base. In another aspect, the present invention provides a method of making an on-body medical device comprising injection molding a plastic base over a flexible fibrous, textured, perforated or porous patch in a mold cavity.

In an embodiment of the present invention, molten plastic is injected into a medical device mold cavity containing the adhesive patch during an injection molding operation, similar to the manner in which in-mold labeling is carried out with other types of products. Unlike an in-mold label, however, the adhesive patch is made of a fibrous, textured, perforated or porous material having many small interstices, openings or cavities into which the plastic material flows during the molding operation. When the plastic material cools and hardens, this creates a very strong bond between the adhesive patch and the medical device without the need for an adhesive.

BRIEF DESCRIPTION OF THE DRAWINGS

Aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up", "down", "bottom", and "top" are relative, and are employed to aid illustration, but are not limiting.

Figure 1:
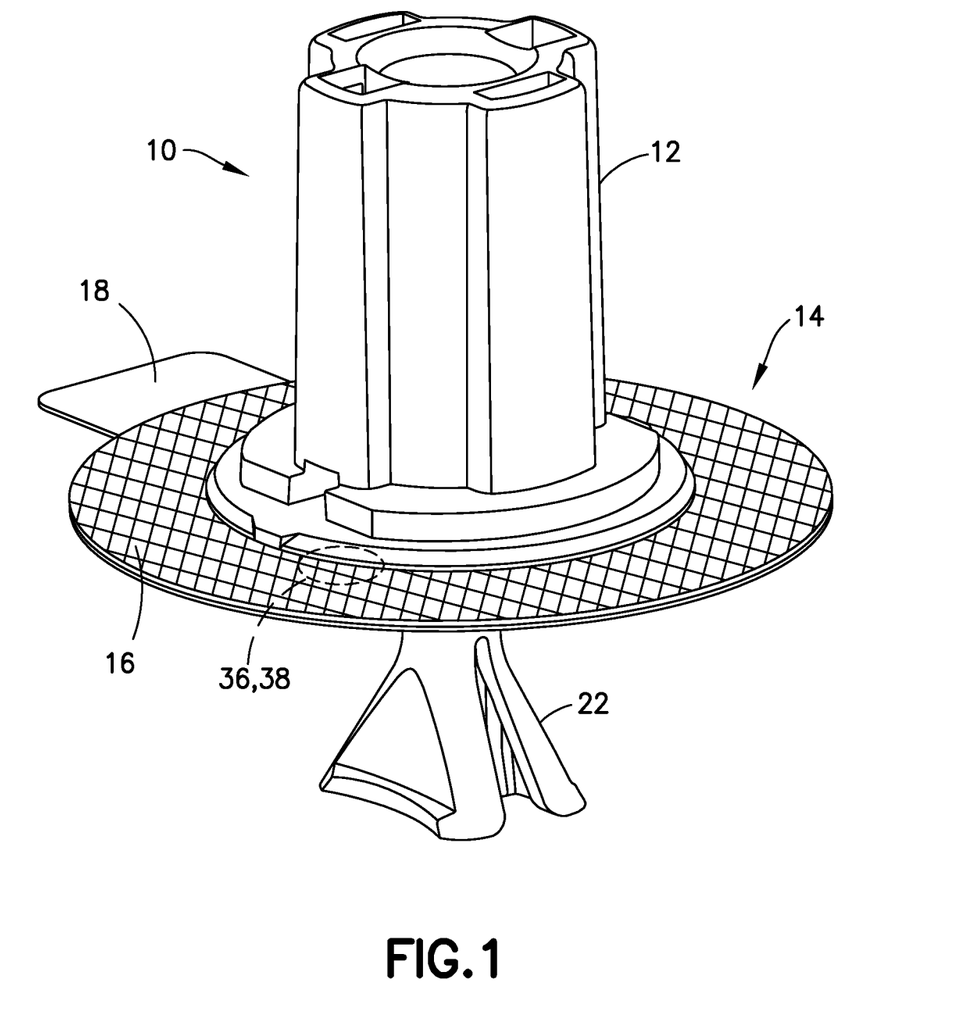
FIG. 1 is a top perspective view of an insulin infusion set having an introducer needle hub, a base assembly with an overmolded adhesive patch, and an introducer needle guard in accordance with an embodiment of the present invention.
Figure 4:
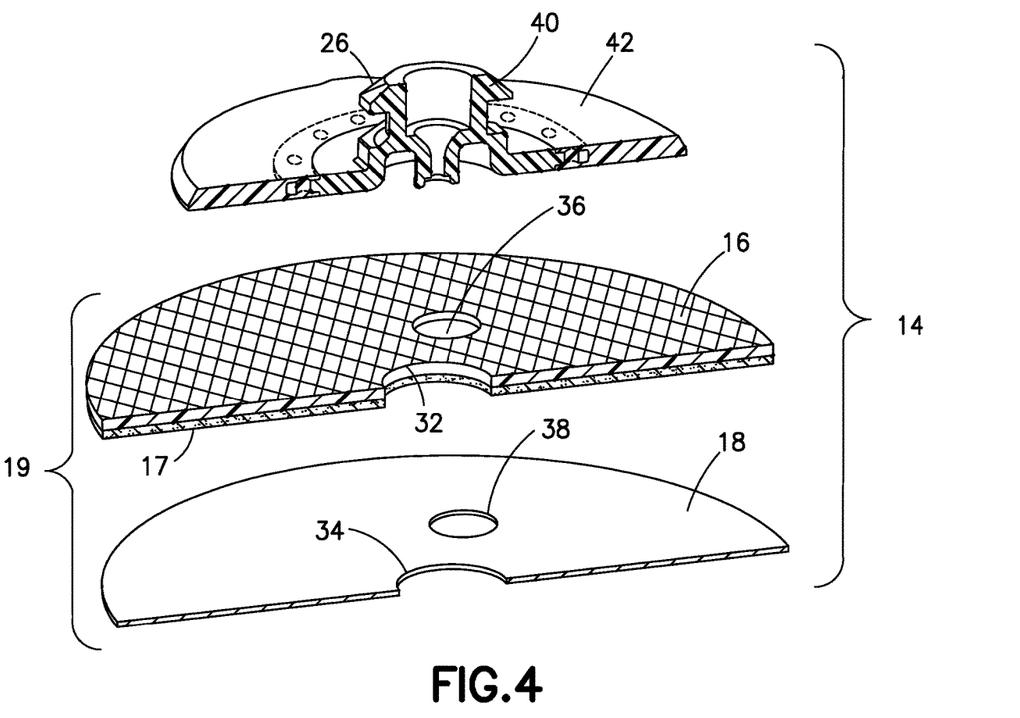
FIG. 4 is a partially exploded perspective view of the infusion set base assembly of FIGS. 2 and 3, with the adhesive patch and release liner shown separately for clarity.

FIG. 1 illustrates an insulin infusion set 10 in accordance with an embodiment of the present invention. The infusion set comprises an introducer needle hub 12 engaged with a base assembly 14. The introducer needle hub 12 also serves as a passive telescopic shield for the introducer needle (not shown) after it is removed. The base assembly 14 includes a flexible patch 16 made of a flexible fibrous, textured, perforated or porous material such as nonwoven medical tape. The patch has an adhesive 17 (visible in FIG. 4) on its underside, which is used to secure the base assembly 14 to the user's skin. A removable backing layer or release liner 18 covers the skin-contacting adhesive 17 prior to use. The patch 16, adhesive 17 and release liner 18 constitute an adhesive patch assembly 19 as shown in FIG. 4.

FIG. 1 illustrates a state in which the introducer needle hub 12 and base assembly 14 are ready to facilitate insertion of a flexible catheter 20 (visible in FIG. 3) and an introducer needle (not shown) into the user. A removable needle guard 22 covers the catheter 20 and the introducer needle (the latter initially received within and protruding from the catheter 20) prior to use.

Figure 2:
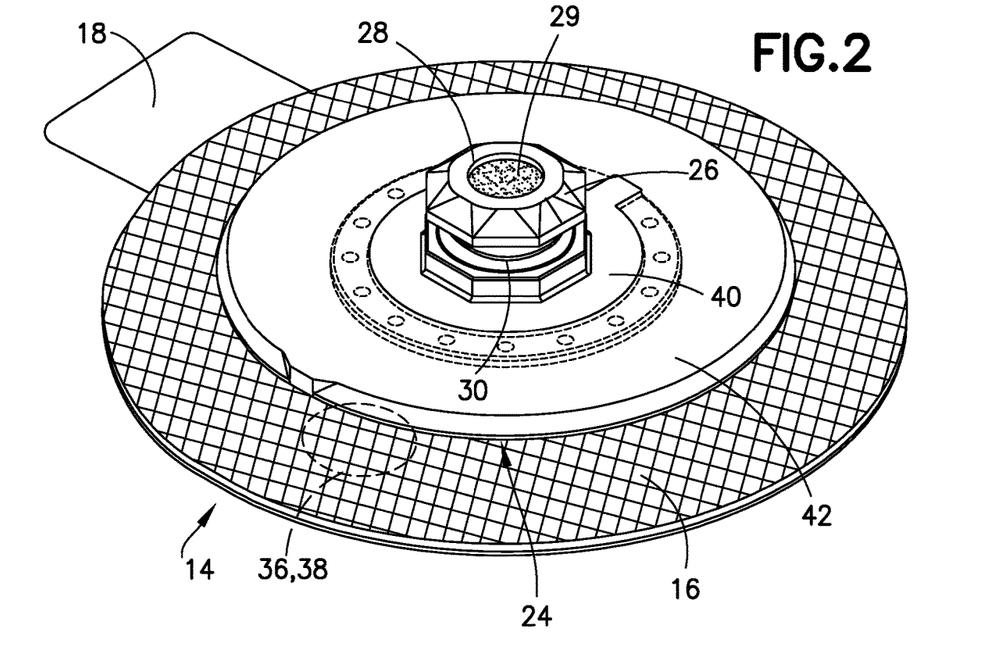
FIG. 2 is a top perspective view of the insulin infusion set of FIG. 1 with its introducer needle hub and introducer needle guard removed, leaving only the base assembly.
Figure 3:
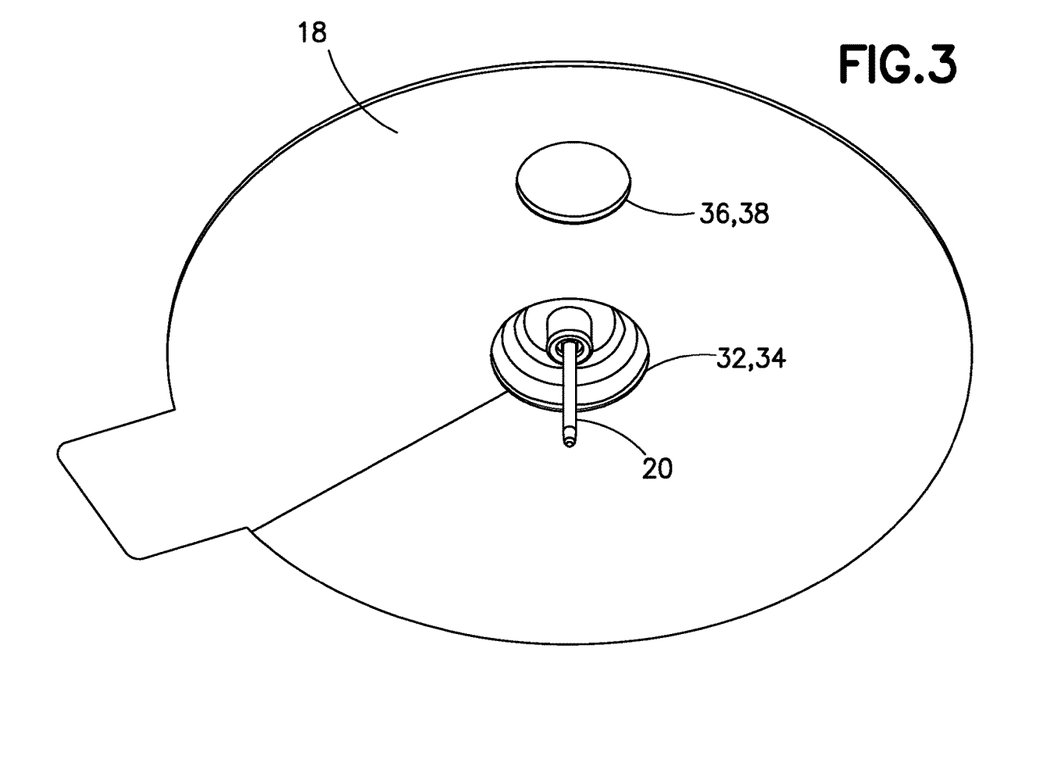
FIG. 3 is a bottom perspective view of the infusion set base assembly of FIG. 2, illustrating the release liner and the flexible catheter that remains in the user's skin after the introducer needle is removed.

FIGS. 2 and 3 illustrate the infusion set 10 with the introducer needle hub 12 and needle guard 22 both removed. With the further removal of the release liner 18 and the with the catheter 20 penetrating into the subcutaneous skin layer, this is how the infusion set 10 would appear when adhered to the user's skin at an infusion site.

As shown in FIG. 2, the base assembly 14 includes a plastic central portion 24 that overlies the flexible adhesive patch 16. The plastic central portion 24 includes an upwardly facing fluid connector 26 having an opening 28 through which insulin is delivered through a pre-slit resilient septum 29 from a compatible fluid coupling (not shown) connected by flexible tubing to an infusion pump (both also not shown). The faceted shape of the fluid connector 26 and the recessed area 30 below its upper face facilitate latching connection with the fluid coupling at discrete rotational positions, allowing the user to position the flexible tubing as desired.

The adhesive patch 16 and release liner 18 are formed with two sets of identical, aligned holes 32, 34 and 36, 38 as shown more clearly in FIG. 4. The holes 32, 34 provide clearance for the emergence of the flexible catheter 20 as shown in FIG. 3. The holes 36, 38 serve as fluid passages for the injection molding process described in more detail hereinafter in connection with FIG. 6.

Figure 5:
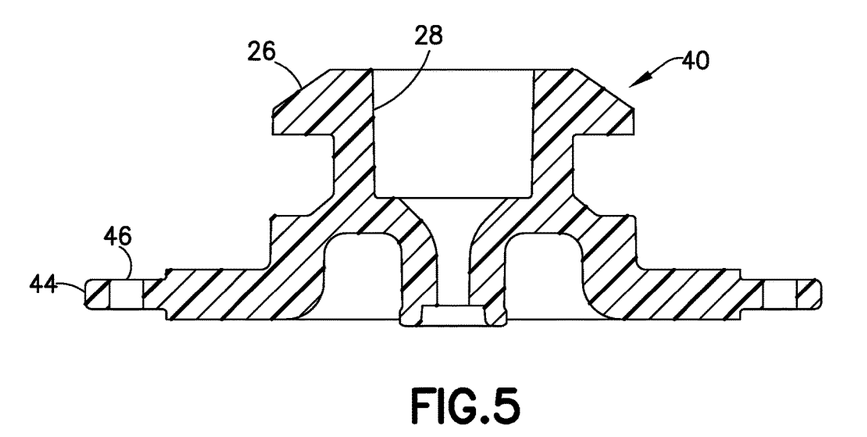
FIG. 5 is a side cross-sectional view of the rigid central portion of the infusion set base assembly of FIGS. 2 and 3 that is formed during the first molding shot of a two-shot injection molding process.

As shown in FIG. 2 and in more detail in FIGS. 4 and 5 (in which the catheter 20 and septum 29 are omitted for clarity), the plastic central portion 24 of the base assembly 14 is made up of two connected parts, a rigid inner hub 40 defining the fluid connector 26 and a somewhat more flexible outer disk 42. Both portions 40, 42 are generally circular in shape when viewed from above. The outermost rim 44 of the rigid inner hub 40 has a reduced thickness in which a plurality of through-holes 46 are formed. The through-holes 46 and the reduced thickness of the rim 44 facilitate bonding between the rigid inner portion 40 and the flexible outer disk 42.

More specifically, the rigid inner hub 40 is injection-molded in a first shot, and the flexible outer disk 42 is molded in a second shot during which the molten plastic material of the outer disk 42 flows around the rim 44 and through the holes 46. The shape of the rim 44 provides a double overlapping joint with the material of the flexible outer disk 42, and the holes 46 provide additional bonding surface area and additional mechanical interlocking.

The flexible outer disk 42 provides improved comfort and mobility of the infusion set base assembly 14 because it moves with the user during physical activity while minimizing contact of the rigid inner hub 40 with the user. The flexible outer disk 42 is attached to the adhesive patch assembly 19 by overmolding during the second shot of the aforementioned two-shot injection molding process.

Figure 6:
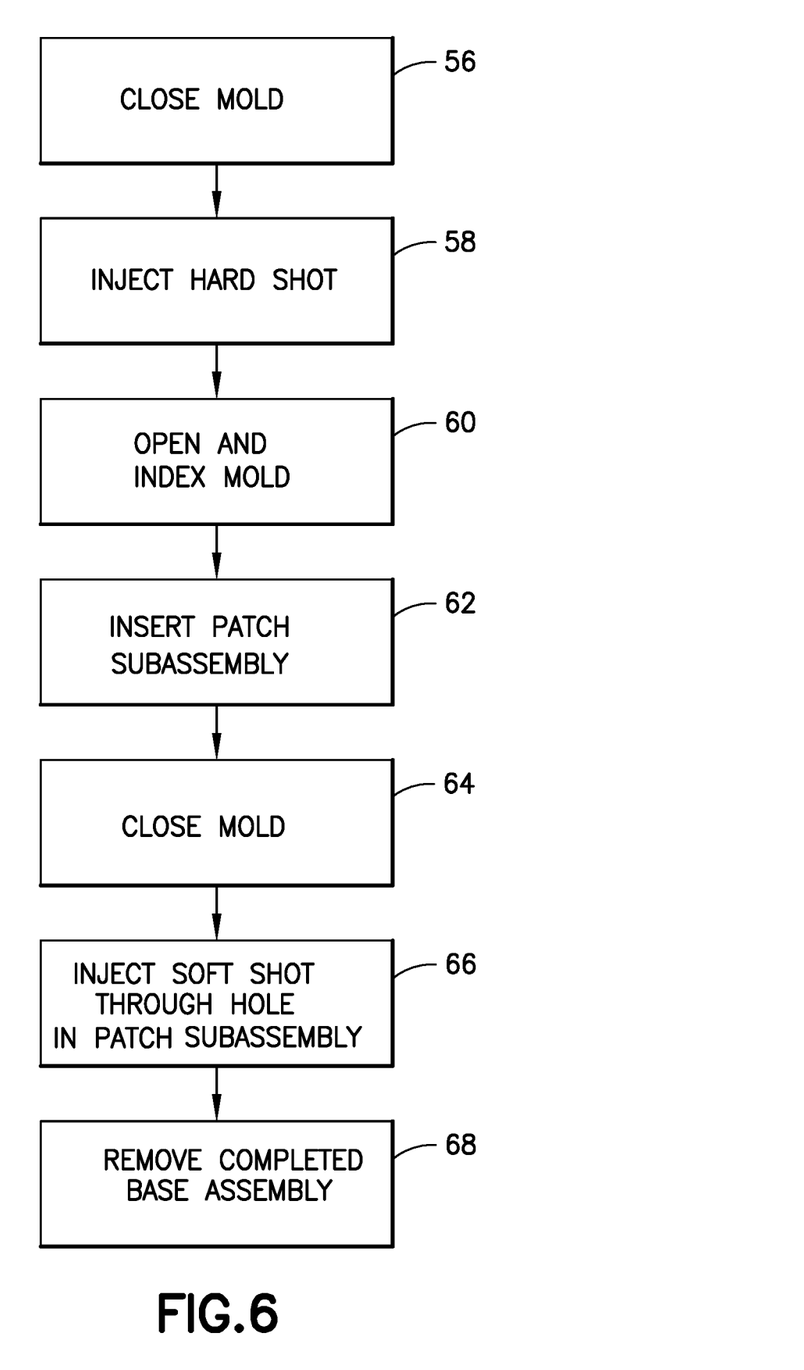
FIG. 6 is a flowchart illustrating the steps of the two-shot injection molding process.
Figure 7:
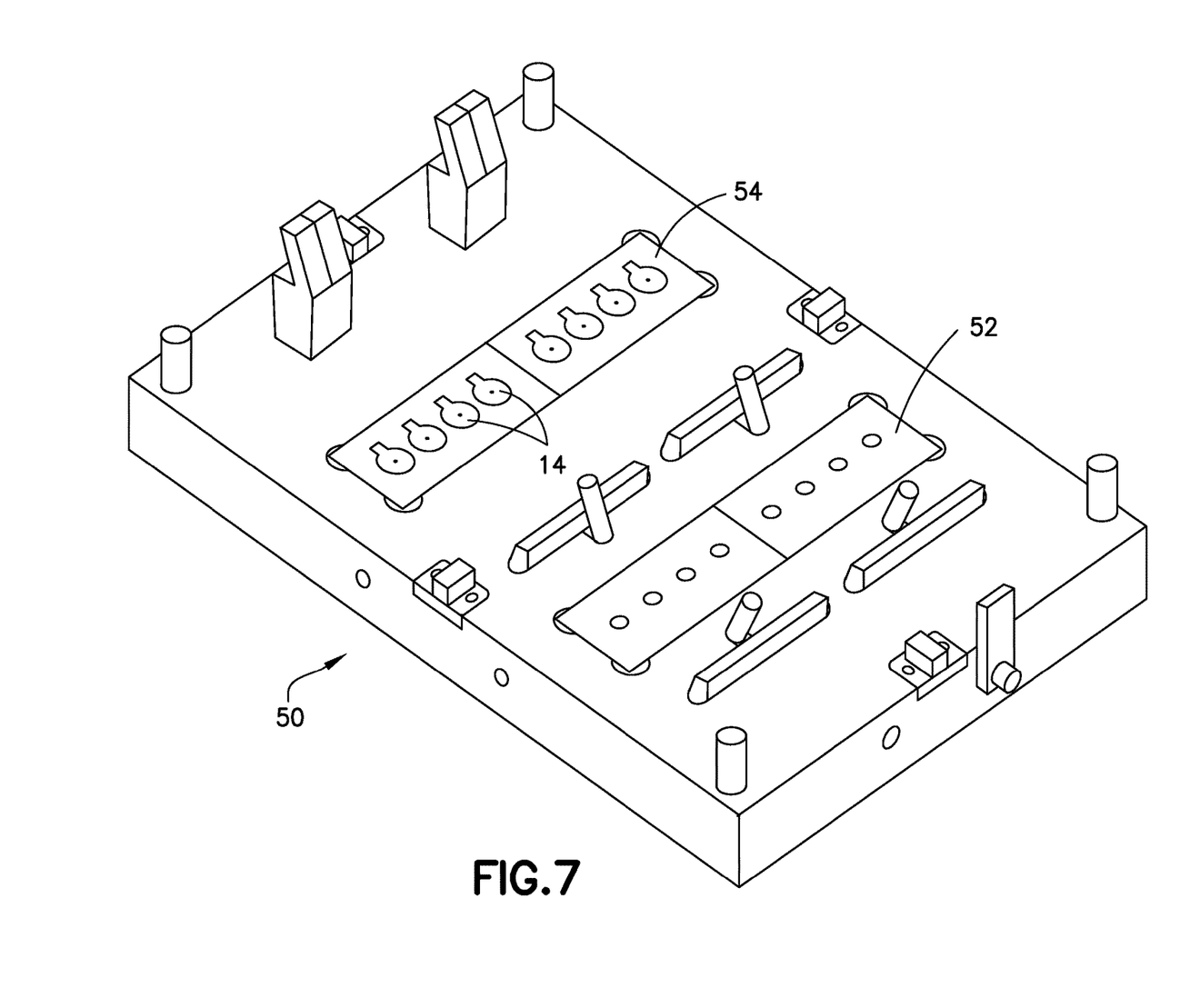
FIG. 7 is a top perspective view of mold tooling that can be used to carry out the two-shot injection molding process of FIG. 6.

The two-shot injection molding process is described in more detail in the flowchart of FIG. 6. The process can be performed using injection mold tooling (only the lower half 50 of which is shown in FIG. 7) having separate sets of mold cavities 52, 54 for the hard and soft shots.

In step 56, the mold is closed (i.e., the upper and lower mold halves are brought together) in preparation for the first (hard) molding shot. This shot forms the rigid inner hubs 40 of FIG. 5.

In step 58, molten plastic material is injected under pressure into the cavities 52 to perform the hard shot. In the illustrated example, eight rigid inner hubs 40 are formed simultaneously during the first molding shot.

In step 60, the mold is opened with the fully formed inner hubs 40 retained in the upper half of the mold. The mold is then indexed by rotating the upper mold half by 180 degrees about a vertical axis with respect to the lower mold half. This aligns the upper mold cavities containing the fully formed inner hubs 40 with the empty lower mold cavities 54 in which the flexible outer disks 42 will be formed and overmolded with the rigid inner hubs 40 in the second (soft) molding shot.

In step 62, robotic end-of-arm tools are used to place the adhesive patch assemblies 19 into the open mold cavities 54 as shown in FIG. 7. The patch assemblies 19 are oriented with their release liners 18 facing downwardly and the exposed surfaces of their adhesive patches 16 facing upwardly into the mold cavity.

In step 64, the mold is again closed in preparation for the second (soft) molding shot. This shot forms the flexible outer disks 42 of FIGS. 2 and 4.

In step 66, the soft molding shot is performed by injecting molten plastic material into the mold cavities 54 from gates (not shown) located beneath the patch assemblies 14. The holes 36, 38 in the adhesive patches 16 and release liners 18 are aligned with these gates. The molten plastic material passes through the holes 36, 38 to form the flexible outer disks 42 in overlying interlocked relationship with the previously formed rigid inner hubs 40 as shown in FIGS. 2 and 4 (to facilitate the proper flow of the molten plastic material, it is preferred that the holes 36, 38 be positioned so that they are at least partially unblocked relative to the hubs 40). At the same time, and with the assistance of the pressure under which the molten plastic material is injected into the mold during the soft shot, the molten plastic material impregnates or permeates the adhesive patches 16 by flowing into the many small interstices, openings or cavities that exist in the material of the patches 16. This creates a strong mechanical bond between the adhesive patches 16 and the flexible outer disks 42 after the injected plastic material has cooled and solidified, without the need for an adhesive. Depending on the specific materials used, a secondary bond can also be formed between the adhesive patches 16 and the rigid inner hubs 40 during the soft shot, thereby strengthening the connection between the adhesive patches 16 and the plastic central portions 24 generally. However, the primary bond is between the adhesive patches 16 and the flexible outer disks 42.

In step 68, the completed base assemblies 14 are removed from the mold for further assembly and packaging steps. This includes the addition of the introducer needle hub 12, catheter 20, needle guard 22 and related components that form the completed infusion set 10 of FIG. 1.

It will be appreciated that the rotational indexing described in step 60 above allows the two sets of mold cavities 52, 54 to be operated simultaneously. This is done in a staggered manner so that hub-forming hard shots are performed on one side of the mold while disk-forming soft shots over previously-formed hubs are performed on the other side of the mold. It will also be appreciated that base assemblies for patch pumps and other types of on-body medical devices can be made using an injection molding process similar to that illustrated in FIG. 6.

In embodiments of the invention, the patch assembly 19 can be die-cut from commercially available 3M™ Medical Nonwoven Tape (Product No. 1776). In this product, the patch material 16 is a ~11.5 mil (0.3 mm) thick white spunlace nonwoven tape made of randomly oriented polyester fibers, the skin-contact adhesive 17 is an acrylate adhesive developed for medical/surgical use, and the release liner 18 is 83 lb. poly-coated Kraft paper of 6 mil (0.15 mm) thickness with a silicone release layer on both sides. Another suitable material is 3M™ Single Coated, Extended Wear Nonwoven Medical Tape (Product No. 4076). Still other materials that can be used are various single-coated medical tapes that are available from the Medical Materials and Technologies division of 3M Company. Other types of fibrous, textured, perforated or porous materials that are able to withstand the heat and pressure of the injection molding process can also be used for the adhesive patch 16 in the practice of the present invention.

In embodiments of the invention, the rigid inner hub 40 and flexible outer disk 42 may be made of any plastic materials that are suitable for injection molding. The rigid inner hub 40 is preferably made from a polyester blended material or polycarbonate, although this is not required. The flexible outer disk 42 is preferably made from a thermoplastic elastic material, some examples of which are listed in the table below Materials which allow for molding of the flexible outer disk 42 at lower temperatures are preferred in order to avoid adverse effects on the skin contact adhesive 17 provided between the patch 16 and the release liner 18.

| # | Material Type | Material Manufacturer | Material # |
|---|---|---|---|
| 1 | TPU | Elastocon | STK-040 |
| 2 | TPE | GLS | Versaflex OM3060 |
| 3 | TPE | GLS | Dynaflex G2711-1000-0 Nat'l |
| 4 | TPE | GLS | OM1040X-1 Nat'l |
| 5 | TPE | GLS | Versaflex HC2110-35N Nat'l |
| 6 | TPE | Tekniplex | Cellene MC2245 |
| 7 | Polyolefin Elastomer | Dow | Engage 8407 |
| 8 | Olefin Block Copolymer | Dow | Infuse 9807 |
| 9 | TPE | Teknor Apex | Medalist MD-46055 NAT XRD1 |

Although only a few embodiments of the present invention have been shown and described, the present invention is not limited to the described embodiments. For example, it may be possible to use compression molding for either or both of the molding steps, instead of injection molding. It will be appreciated by those skilled in the art that other changes may also be made to the disclosed embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

What is claimed is:

1. A method of making an on-body medical device comprising injection molding a plastic base over a flexible fibrous, textured, perforated or porous patch in a mold cavity, said patch having a first hole, wherein the plastic base is provided with a fluid connector on a first side of said base and having an opening extending through said base, said fluid connector configured for receiving a liquid medicament and for receiving a cannula on a second side of said base for delivering said liquid medicament into the skin of a patient though said first hole in said patch.

2. The method of claim 1, wherein the flexible fibrous, textured, perforated or porous patch is preformed and is placed in the mold cavity prior to the injection molding of the base.

3. The method of claim 2, wherein a plastic material injected into the mold cavity to form the base is injected through a second hole in the patch spaced from the first hole.

4. A method of making an on-body medical device comprising injection molding a plastic base over a flexible fibrous, textured, perforated or porous patch in a mold cavity, wherein the flexible fibrous, textured, perforated or porous patch is preformed and is placed in the mold cavity prior to the injection molding of the base, and wherein the patch includes a release liner.

5. The method of claim 4, wherein a plastic material injected into the mold cavity to form the plastic base passes through aligned holes in the patch and release liner.

6. The method of claim 1, wherein said base and said patch are secured to each other at an interface that is substantially free of an adhesive.

7. The method of claim 1, wherein the fluid connector comprises a septum in said opening.

8. The method of claim 1, wherein said fluid connector faces upwardly from said first side of said base, and a second side of said base is overmolded with said flexible fibrous, textured, perforated or porous patch.

9. The method of claim 1, wherein said plastic base is molded on a first side of said patch, and said method further comprising injecting a plastic material though a hole from a second side of said patch to form said plastic base.

10. The method of claim 1, wherein said method further comprises molding a first portion of said base, positioning a first side of the patch against the molded first portion of the base, and injecting a plastic material onto the first portion and the first side of the patch to form a second portion of the base attached to the first portion, where said plastic material is injected through a second hole in said patch to form said second portion.

11. The method of claim 10, wherein said first portion is rigid and said second portion is flexible.

12. The method of claim 10, wherein said plastic material is injected through a second hole in said patch from a second side of said patch.

13. A two-shot injection molding method for making an on-body medical device, comprising:
   during a first injection molding shot, molding a first portion of a base;
   after the first injection molding shot, placing a preformed flexible fibrous, textured, perforated or porous patch into a mold cavity with the molded first portion of the base; and
   during a second injection molding shot, overmolding a second portion of a base with the patch in the mold cavity where a second injection molding shot is injected through a hole in the patch to form said second portion;
   wherein the base is provided with a fluid connector on a first side of said base for receiving a liquid medicament and for receiving a cannula on a second side of said base for delivering said liquid medicament into the skin of a patient.

14. A two-shot injection molding method for making an on-body medical device, comprising:
   during a first injection molding shot, molding a first portion of a base;
   after the first injection molding shot, placing a preformed flexible fibrous, textured, perforated or porous patch into a mold cavity with the molded first portion of the base; and
   during a second injection molding shot, overmolding a second portion of a base with the patch in the mold cavity;
   wherein the patch includes a release liner.

15. The method of claim 14, wherein a plastic material injected into the mold cavity to form the second portion of the base passes through aligned holes in the patch and release liner.

16. The method of claim 13, wherein said base and said patch are secured to each other at an interface that is substantially free of an adhesive.

17. The method of claim 13, wherein the fluid connector comprises a septum in said opening.

18. The method of claim 13, wherein said first portion of said base is rigid and said second portion of said base is flexible.

19. The method of claim 13, wherein the first portion of the base is oriented on a first side of the base and said second shot is injected through said hole from a second side of the patch opposite said first portion of said base.

* * * * *